(12) United States Patent
Morrison et al.

(10) Patent No.: US 8,991,389 B2
(45) Date of Patent: Mar. 31, 2015

(54) DRUG SOLUTION LEVEL SENSOR FOR AN ULTRASONIC NEBULIZER

(75) Inventors: Mark Morrison, Basking Ridge, NJ (US); Eric A. Lieberman, Scotch Plains, NJ (US); Lakshmi Penugonda, Piscataway, NJ (US)

(73) Assignee: RIC Investments, LLC, Wilmington, DE (US)

( * ) Notice: Subject to any disclaimer, the term of this patent is extended or adjusted under 35 U.S.C. 154(b) by 1759 days.

(21) Appl. No.: 11/787,274

(22) Filed: Apr. 16, 2007

(65) Prior Publication Data

US 2007/0277816 A1   Dec. 6, 2007

Related U.S. Application Data

(60) Provisional application No. 60/793,447, filed on Apr. 20, 2006, provisional application No. 60/793,448, filed on Apr. 20, 2006, provisional application No. 60/793,351, filed on Apr. 20, 2006.

(51) Int. Cl.
| | | |
|---|---|---|
| *A61M 11/04* | (2006.01) | |
| *A61M 15/00* | (2006.01) | |
| *A61M 11/00* | (2006.01) | |
| *B05B 17/06* | (2006.01) | |

(52) U.S. Cl.
CPC ......... *A61M 11/005* (2013.01); *A61M 15/0085* (2013.01); *B05B 17/0615* (2013.01); *A61M 15/0036* (2014.02); *A61M 15/0043* (2014.02); *A61M 2205/18* (2013.01); *A61M 2205/276* (2013.01); *A61M 2205/3386* (2013.01); *A61M 2205/3389* (2013.01); *A61M 2205/581* (2013.01); *A61M 2205/583* (2013.01)
USPC ................. 128/200.16; 128/200.14; 239/370; 239/338; 239/102.2

(58) Field of Classification Search
USPC ............ 128/200.16, 200.18, 200.21, 200.24, 128/203.12, 203.14, 203.15, 203.26, 128/203.27, 202.21, 200.14, 200.23; 239/102.1, 102.2
See application file for complete search history.

(56) References Cited

U.S. PATENT DOCUMENTS

| | | | | |
|---|---|---|---|---|
| 4,113,809 | A * | 9/1978 | Abair et al. ..................... 261/81 |
| 7,040,549 | B2 * | 5/2006 | Ivri et al. ................. 128/200.16 |
| 2003/0196660 | A1 * | 10/2003 | Haveri ..................... 128/203.12 |
| 2006/0201500 | A1 | 9/2006 | Von Hollen et al. |
| 2006/0243274 | A1 | 11/2006 | Von Hollen et al. |

FOREIGN PATENT DOCUMENTS

WO   WO 2004/017848   3/2004

* cited by examiner

*Primary Examiner* — Victoria J Hicks
*Assistant Examiner* — Kari Petrik (57) ABSTRACT

A nebulizer includes a piezoelectric transducer for aerosolizing a drug solution in a disposable cup module disposed above the transducer. Acoustic waves generated by the transducer propagate sequentially through transmitting medium, a first barrier, coupling medium, and a second barrier that forms part of the cup module, and into the interior of the cup module. The transducer at least partially comprises silver. The silver fluidly contacts the transmitting medium to discourage bacteria growth in the transmitting medium. The device includes electronics components that drive the transducer and measure an electrical characteristic associated with the transducer during operation. The electronics components measures changes in the electrical characteristic to determine when the drug solution level falls below a predetermined threshold, and deactivates the device accordingly.

DRUG SOLUTION LEVEL SENSOR FOR AN ULTRASONIC NEBULIZER

CROSS-REFERENCE TO RELATED APPLICATIONS

This application claims priority under 35 U.S.C. §119(e) from U.S. Provisional Patent Application No. 60/793,447, entitled "Drug Solution Level Sensor for an Ultrasonic Nebulizer" and filed on Apr. 20, 2006; U.S. Provisional Patent Application No. 60/793,448, entitled "Disposable Drug Solution Cup for an Ultrasonic Nebulizer" and filed on Apr. 20, 2006; and U.S. Provisional Patent Application No. 60/793,351, entitled "Ultrasonic Nebulizer with Metal Coated Ultrasonic Generator" and filed on Apr. 20, 2006. The aforementioned applications are hereby incorporated by reference herein in their entirety for all purposes.

BACKGROUND OF THE INVENTION

1. Field of the Invention

The present invention relates to nebulizers, and more particularly to devices and methods for detecting the level of a drug solution in a nebulizer.

2. Description of the Related Art

Various nebulizers include sensors that sense when the drug solution chamber is empty, thereby signaling that the drug has been completely delivered. For example, U.S. patent application Ser. No. 11/367,486 (now U.S. Publication No. 2006/0201501) and Ser. No. 11/367,075 (now U.S. Publication No. 2006/0243274), both of which were filed Mar. 3, 2006, disclose the use of a probe in a drug solution chamber. The probe detects an AC signal that passes from an acoustic wave generator through the liquid drug to the probe. When the drug level falls below the probe, the circuit is interrupted, thereby indicating that the drug level is below the level of the probe. One potential drawback to this system is that such drug level sensors are disposed within the drug solution chamber in direct contact with the drug solution. In addition, the effectiveness of such probe-based drug level sensors relies upon the ability of the drug solution to conduct the A/C signal to the probe.

SUMMARY OF THE INVENTION

An aspect of one or more embodiments of the present invention provides a method of sensing when an amount of drug solution in a nebulizer falls below a threshold value by measuring a change in an electrical characteristic (e.g., impedance, resonant frequency, an electrical characteristic indicative of impedance, etc.) of a piezoelectric transducer used to aerosolize the drug solution. The measurement may be used to determine completion of the treatment and accordingly deactivate the nebulizer and/or indicate treatment completion to the patient.

Another aspect of one or more embodiments of the present invention provides a nebulizer that includes a drug solution container for holding a drug solution therein, a piezoelectric transducer connected to the drug solution container, and electronics components electrically connected to the transducer. The electronics components are constructed and arranged to provide A/C current to the transducer to drive the transducer. The electronics components include a sensor for measuring an electrical characteristic associated with the transducer during operation.

The electronics components may turn off the transducer when the measured electrical characteristic reaches a predetermined value. Additionally or alternatively, the electronics components may turn off the transducer in response to the measured electrical characteristic varying by more than a predetermined amount over a predetermined time period.

Another aspect of one or more embodiments of the present invention provides a method of using a nebulizer. The method includes operating a piezoelectric transducer to generate acoustic waves to aerosolize a liquid, and measuring an electrical characteristic (e.g., impedance, resonant frequency, an electrical characteristic indicative of impedance) of the transducer. The method may also include ceasing operation of the transducer in response to the measured electrical characteristic reaching a predetermined value. The method may include ceasing operation of the transducer in response to sensing abrupt changes in the electrical characteristic. The method may include measuring a rate of variation of the electrical characteristic associated with the transducer. The method may further include ceasing operation of the transducer when the rate of variation exceeds a predetermined value. The method may include ceasing operation of the transducer in response to the measured electrical characteristic varying by more than a predetermined amount over a predetermined time period.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of"a", "an", and "the" include plural referents unless the context clearly dictates otherwise.

BRIEF DESCRIPTION OF THE DRAWINGS

FIG. 1 is side cross-sectional view of a nebulizer according to an embodiment of the present invention;

FIG. 2 is a front cross-sectional view of the nebulizer in FIG. 1;

FIG. 3 is a front, unassembled, partial, cross-sectional view of a cup module and cup support of the nebulizer in FIG. 1;

FIG. 4 is a front, partial view of a cup module and aerosol generator module of a nebulizer according to an alternative embodiment of the present invention;

FIG. 5 is a front cross-sectional view of a cup module according to an alternative embodiment of the present invention;

FIG. 6 is a schematic view of an impedance sensor of the nebulizer in FIG. 1;

FIG. 7 is a schematic view of a liquid level sensor according to an alternative embodiment of the present invention; and FIG. 8 is a schematic view of a liquid level sensor according to an alternative embodiment of the present invention.

DETAILED DESCRIPTION OF THE EXEMPLARY EMBODIMENTS

FIGS. 1-3 illustrate a handheld nebulizing drug delivery device 10 according to an embodiment of the invention. The device 10 includes a housing 20. While the housing 20 can be a unitary structure, in one embodiment, and as illustrated, the device 10 may be formed from four modules, including a mouthpiece module 30, a cup module 40, an ultrasonic wave generating module 50, and a base module 60 that can be coupled and decoupled from one another.

Further details of this arrangement can be appreciated from U.S. patent application Ser. No. 11/367,486 (now U.S. Publication No. 2006/0201501) and Ser. No. 11/367,075 (now U.S. Publication No. 2006/0243274), both of which were filed Mar. 3, 2006 and are hereby incorporated by reference in their entirety.

Figure 1:
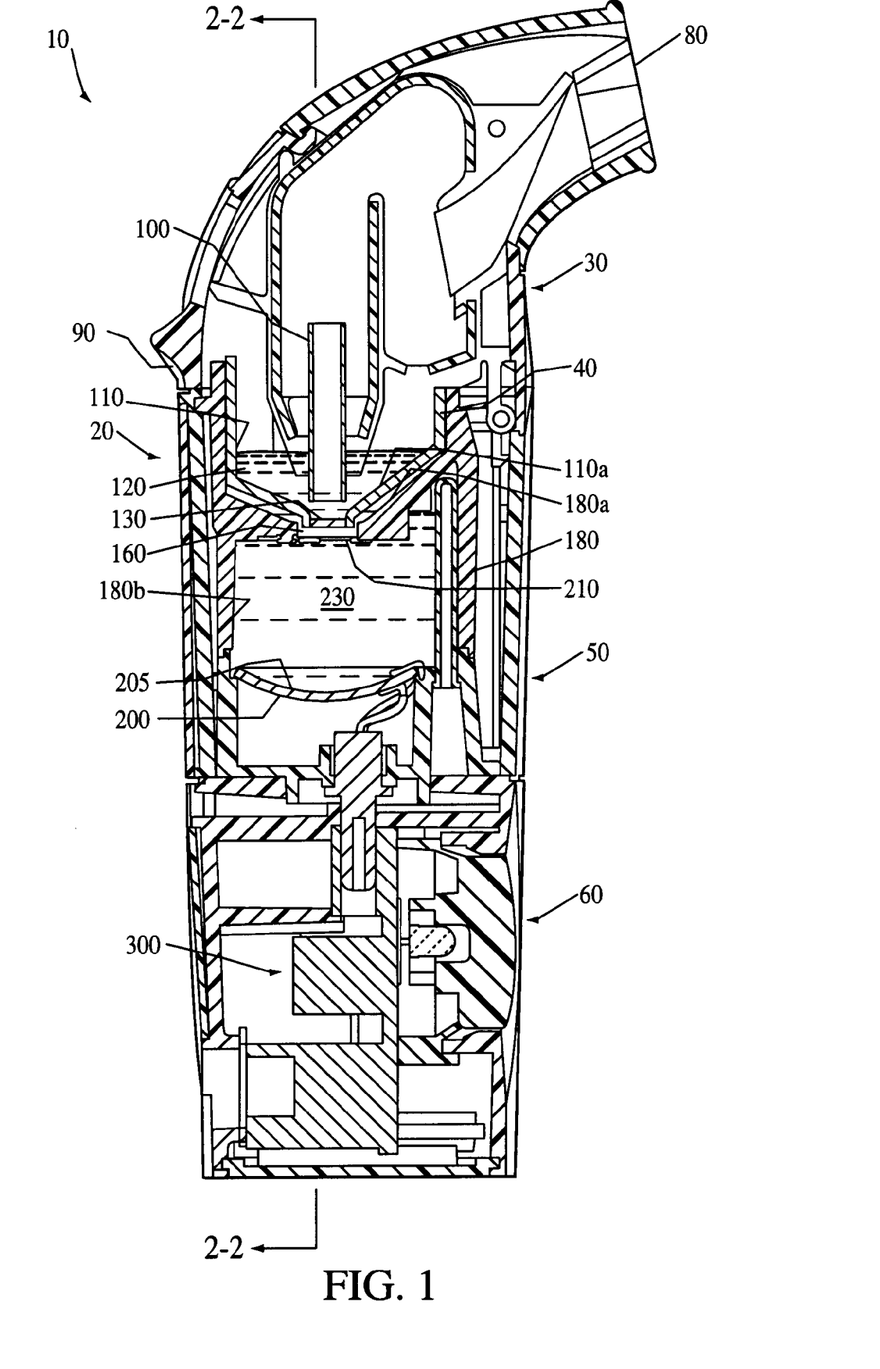

As shown in FIG. 1, the mouthpiece module 30 generally functions to deliver nebulized drug solution particles to a user through an outlet port 80. Atmospheric air is drawn into the housing 20 through an air inlet port 90 formed on the rear of the mouthpiece module 30. The mouthpiece module 30 includes a guide tube 100 to direct a stream of drug solution 120, as described below. Prior to delivery of nebulized drug solution particles via the outlet port 80, the mouthpiece module 30 has internal structure that separates larger drug solution droplets from the nebulized particles that are delivered to the user and returns such larger droplets to a drug solution reservoir/container 110 formed by the cup module 40.

The cup module 40 includes the reservoir/container 110 that is adapted to contain a metered dose of the liquid drug solution 120. The container 110 comprises a first main material such as plastic. The container 110 also includes a thin barrier 130 connected to the main material at a base of the container 110. The barrier 130 permits acoustic waves to pass therethrough and be transmitted to the drug solution reservoir 110 and drug solution 120.

Figure 3:
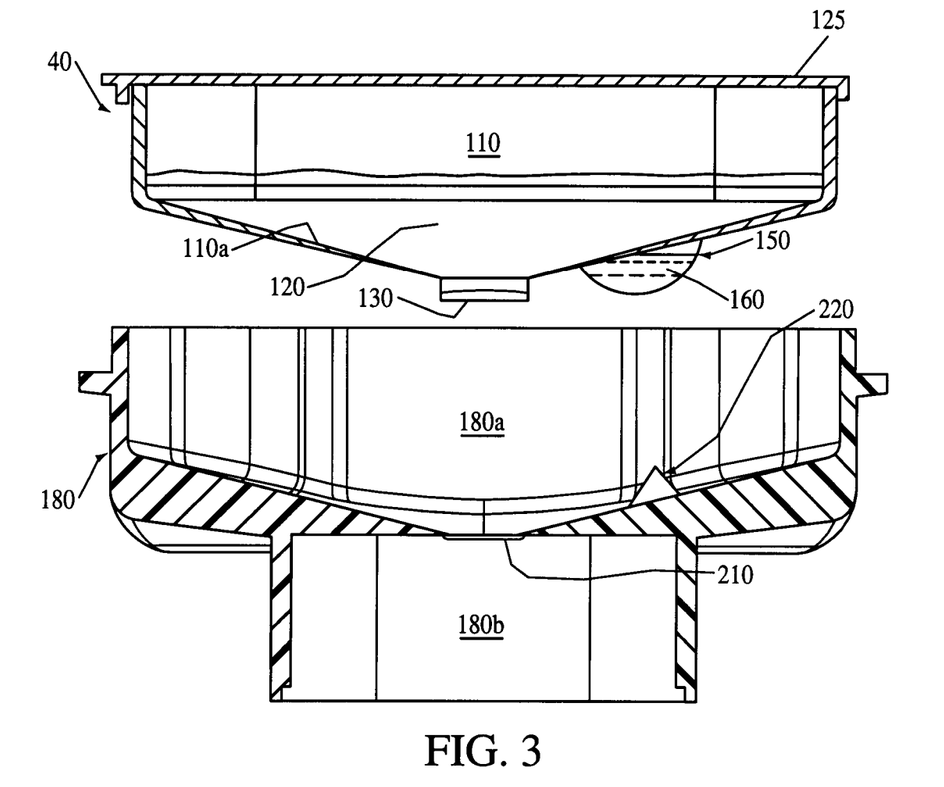

As shown in FIG. 3, the metered dose of drug solution 120 may be prepackaged with the cup module 40. To use the cup module 40, a protective seal 125 is pealed away or otherwise unsealed (e.g., cut, broken, torn along perforations, etc.) from the cup module 40 to expose the drug solution 120. The protective seal 125 may be removed before or after connecting the cup module 40 to the remainder of the device 10. The illustrated seal 125 is constructed and arranged to be manually removed/unsealed. According to an alternative embodiment of the present invention, attachment of the mouthpiece module 30 to the device 10 breaks the seal 125 (e.g., via interaction between the seal 125 and a sharp projection or sharp edge of the guide tube 100 of the mouthpiece module 30).

While the drug solution 120 is prepackaged with the cup module 40 in the illustrated embodiment, the drug solution 120 may alternatively be added to the cup module 40 immediately before use of the device 10 without deviating from the scope of the present invention.

The reservoir 110 is preferably shaped to direct drug solution 120 toward the barrier 130 as the level of drug solution in the reservoir 110 drops as a result of aerosolization of the drug solution 120. In the illustrated embodiment, the sides 110a of the reservoir 110 slope inwardly toward the barrier 130 as the sides progress downwardly. Alternatively, the sides may comprise any other suitable shape (e.g., vertical walls, frustaconical shape, etc.) without deviating from the scope of the present invention.

Figure 2:
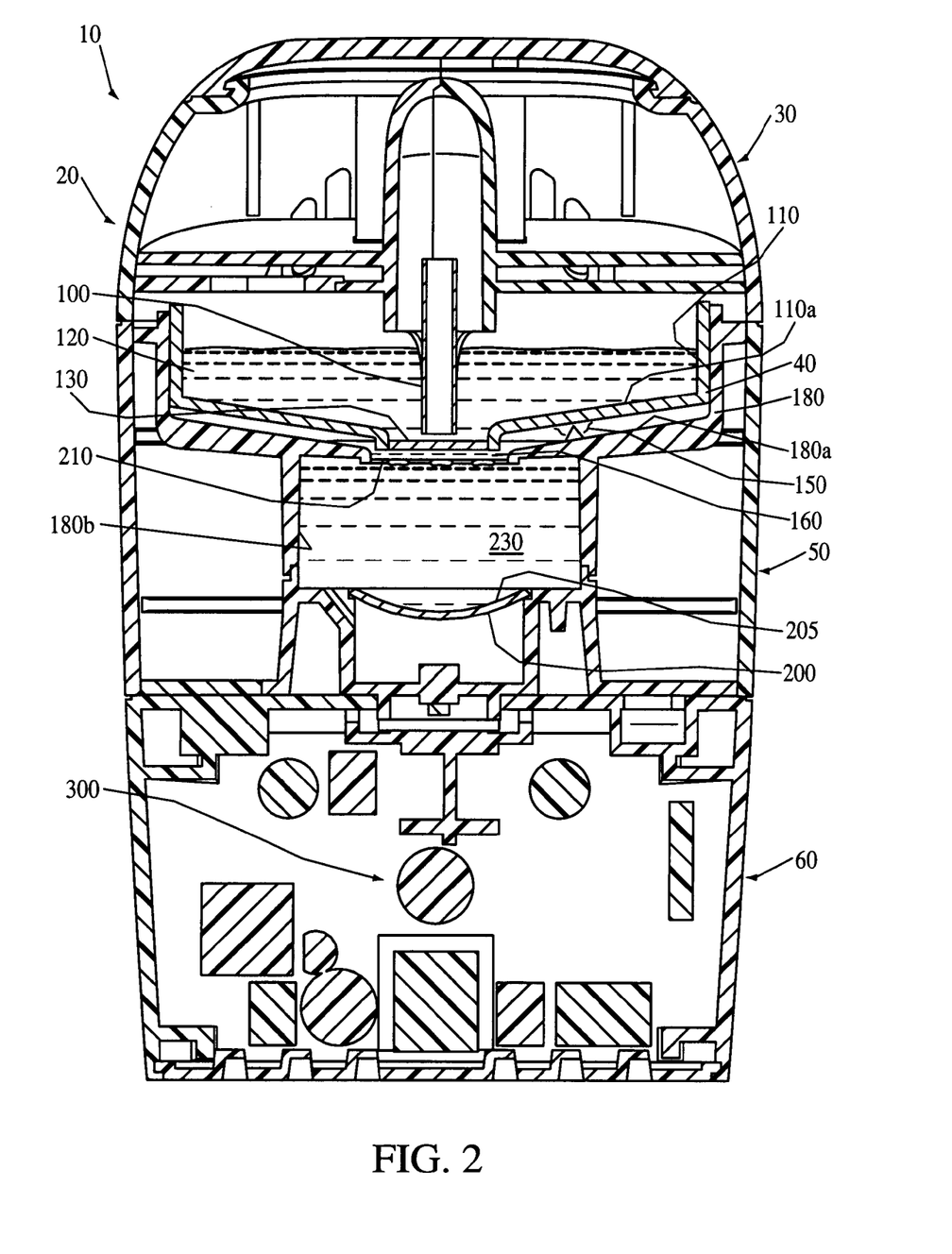

As shown in FIGS. 2 and 3, the cup module 40 includes a rupturable capsule 150 disposed on a lower exterior side of the reservoir 110. As shown in FIG. 3, the capsule 150 contains coupling medium 160 that is designed to transmit acoustic waves therethrough.

As shown in FIGS. 1 and 2, the ultrasonic wave generating module 50 comprises a cup support 180 and an aerosol generator 200.

The cup support 180 defines upper and lower containers 180*a*, 180*b* that are separated and sealed from each other by a thin barrier 210, which permits acoustic waves to pass therethrough between the containers 180*a*, 180*b*. A sharp protrusion 220 is disposed in the upper container 180*a*. The upper container 180*a* and cup module 40 have complimentary shapes such that the cup module 40 may be inserted into the container 180*a*, as shown in FIGS. 1 and 2. The capsule 150 and sharp protrusion 220 are aligned such that insertion of the cup module 40 into the cup support 180 causes the sharp protrusion 220 to rupture the capsule 150 and release the coupling medium 160.

The upper container 180*a* is preferably shaped to direct the coupling medium 160 from the ruptured capsule 150 toward the barrier 210. In the illustrated embodiment, sides of the container 180*a* slope inwardly toward the barrier 210 as the sides progress downwardly. Alternatively, the sides may comprise any other suitable shape (e.g., vertical walls, frustaconical shape, etc.) without deviating from the scope of the present invention. As shown in FIGS. 1 and 2, the coupling medium 160 is preferably voluminous enough to completely fill a gap formed between the barriers 130, 210 when the cup module 40 is inserted into the container 180*a*. The cup module 40 and cup support 180 are preferably shaped so as to minimize the gap between the barriers 130, 210, thereby minimizing the volume of coupling medium 160 required to fill the gap. Presence of the coupling medium 160 between the barriers 130, 210 facilitates propagation of acoustic waves between the barriers 130, 210, as described below.

The barriers 130, 210 may comprise any suitable material that prevents fluid flow therethrough while permitting transmission of acoustic waves therethrough. The barriers 130, 210 may be formed, for example, by being stamped from a roll of material. The barriers 130, 210 may be stamped into a generally circular shape, or may have any other suitable shape. According to one embodiment of the present invention, the barriers 130, 210 each have a thickness that is less than or equal to 0.0005 inches and greater than 0.0001 inches. The barriers 130, 210 may comprise polyetheretherketone (PEEK), or other suitable materials.

In the embodiment illustrated in FIGS. 1 and 2, the acoustic wave generator 200 comprises a concave piezoelectric transducer 200 disposed in the lower container 180*b*. The lower container 180*b* is sealed and filled with a transmitting medium 230 that is designed to transmit acoustic waves. The piezoelectric transducer 200 generates acoustic waves at a generator frequency, such as, in a non-limiting example, 2.5 MHz. The acoustic waves are focused by the concave configuration of the piezoelectric transducer 200 at a focal point that is within drug solution reservoir 110, adjacent to or at the bottom of the guide tube 100, as described below.

The acoustic wave generator 200 may have additional or alternate structural and functional characteristics as described in International Application No. PCT/AU2003/001079 (International Publication Number WO 2004/017848), hereby incorporated by reference in its entirety, and U.S. patent application Ser. No. 11/367,486 (now U.S. Publication No. 2006/0201501) and Ser. No. 11/367,075 (now U.S. Publication No. 2006/0243274).

The base module 60 generally contains device electronics 300 and has a control interface, such as a manually operable button to enable the user to activate the device 10. The device electronics 300 operatively connect to the piezoelectric transducer 200 to energize the transducer 200. According to an embodiment of the present invention, the device electronics deliver A/C current to the transducer 200 to drive the transducer 200 at a frequency, e.g., 2.5 MHz.

The device electronics 300 also include a drug solution liquid level sensor to sense when the drug solution 120 level is low or empty. The drug solution liquid level sensor comprises an impedance sensor 310 that operatively connects to the transducer 200 to detect an impedance of the transducer 200. The impedance of the transducer 200 changes based on, among other things, the weight of the medium 230, 160 and drug solution 120 pressing on the surface of the transducer 200, the presence or absence of drug solution 120 in the container 110, etc. Consequently, the impedance varies with the amount of drug solution 120 disposed in the cup module 40. When the drug solution 120 level becomes low, the drug solution 120 may begin to sputter, which causes rapid changes in the impedance of the transducer 200. The device electronics 300 senses the impedance change to determine when the drug solution 120 is nearly empty or sputtering.

The device electronics 300 may use the impedance sensor 310 solely to measure when the drug solution 120 level is low, for example, by sensing abrupt changes in the impedance that result from sputtering of the drug solution 120. According to one embodiment, the device electronics 300 takes a predetermined number of impedance measurements (e.g., 1, 2, 3, 4, etc.) during a predetermined time period (e.g., 1 second) and averages the measured impedances. The measurements may be evenly spaced over the time period or be lumped together (e.g., one second time period; four measurements taken at 65 microseconds intervals). The device electronics 300 then compares the average impedance to the average impedance measured during the previous time period's sample. If the impedance change exceeds a predetermined value (i.e., the sample-based rate of change of the impedance exceeds a predetermined value), the device electronics 300 concludes that the drug solution 120 is low or empty. This dynamic impedance deviation calculation is independent of the absolute baseline impedance of the transducer 200, which, as described below, may vary widely from device 10 to device 10 or transducer 200 to transducer 200. In addition, the baseline impedance may drift over time.

While the above-described embodiment functions on a binary scale to determine the presence or absence of drug solution 120, the device electronics 300 may alternatively or additionally use the impedance sensor 310 to proportionally measure the drug solution 120 level. The device electronics 300 may use the measured drug solution level to indicate drug delivery progress to the patient (e.g., as a percentage of drug delivery completion) or record drug delivery progress in an associated memory.

In one embodiment, when the device electronics 300 senses that the drug solution 120 level is low, the device electronics 300 automatically deactivates the acoustic wave generator 200. Deactivating the generator 200 may prevent the adverse heating of the barrier 130 or the remaining drug solution 120, which might otherwise occur if the generator 200 continues to ultrasonically excite a reduced volume of drug solution 120. Additionally or alternatively, the device electronics 300 may activate an alert, such as, for example, a visual or audible indicia, that may warn the user that the drug solution 120 has dropped below a threshold level, thereby indicating completion of the drug delivery cycle. Additionally or alternatively, the device electronics 300 may sense the impedance at the beginning of a treatment to determine if drug solution 120 was properly placed in the device 10, and cease the treatment if no drug solution 120 is detected.

Figure 6:
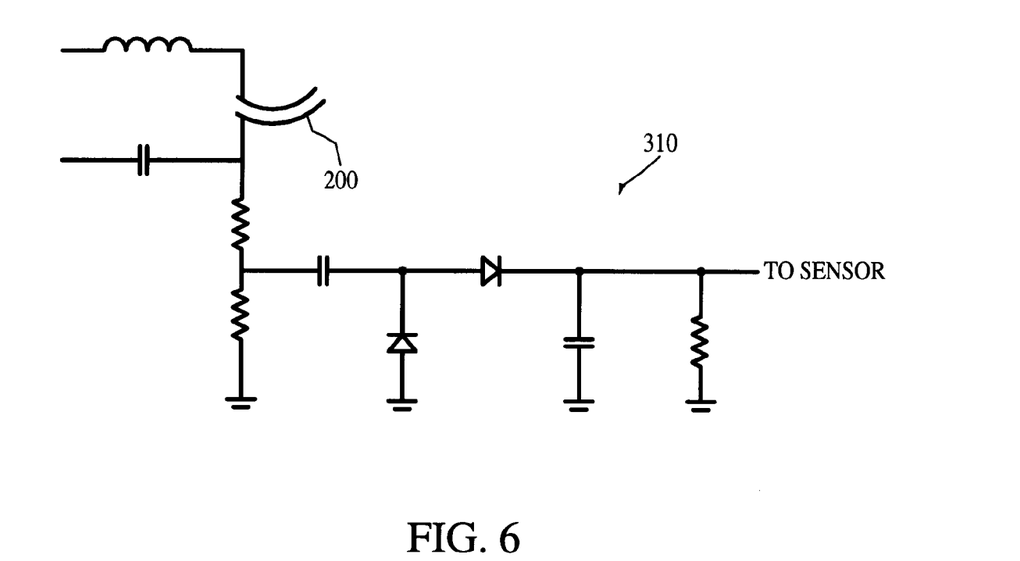

Regarding the impedance sensor 310, it will be appreciated that any suitable device may be used to directly or indirectly determine the impedance of the transducer 200. FIG. 6 illustrates an exemplary impedance sensor 310. The transducer 200 may be considered a resistor at resonance. The resistor is driven by a series resonant circuit consisting of an inductor on one side and a capacitor on the other. The values chosen for these components preferably make them resonant at or near the resonant frequency of the transducer 200 (e.g., ~2.5 MHz). In the depicted embodiment, these three components are arranged in an impedance divider configuration. Under normal circumstances, the voltages across each of these components would divide proportionally according to the current through each, which is identical in a series circuit. However, because the transducer 200 behaves as a non-linearly variable resistor whose impedance changes as described above, changes in the transducer 200 impedance effects changes in the current through all three components, thereby providing a change in the voltage through the circuit. The voltage observed at the capacitor/transducer 200 is a periodic oscillation that approximates a sine wave. The device electronics 300 rectifies and filters the voltage signal to simplify monitoring of changes in the transducer 200 impedance, which, as described above, are associated with the amount of drug solution 120 in the cup module 40. By sensing impedance as a function of time (e.g., 1 second sampling), the sensor 310 can detect rapid voltage (and impedance) changes associated with sputter to determine when the drug solution 120 level is low.

While the embodiment illustrated in FIG. 6 utilizes an impedance divider configuration to indirectly sense the impedance by virtue of monitoring voltage changes, the impedance sensor 310 may alternatively comprise any other suitable mechanism for sensing the impedance of the transducer 200 without deviating from the scope of the present invention. For example, the device electronics 300 may sense the impedance of the transducer 200 by monitoring any electrical characteristic (e.g., current, voltage, frequency, phase, etc.) that is indicative of the impedance of the transducer 200. For example, an alternative impedance sensor may comprise a Wheatstone bridge, in which a measured voltage across the bridge is indicative of the impedance of the transducer 200. Alternatively, the current through the transducer 200 and voltage across the transducer 200 may be measured and the impedance calculated as a quotient of the two quantities (i.e., $Z=E/I$). As such, the impedance sensor may utilize any suitable combination of circuit components and configurations to measure the electrical characteristic (e.g., voltage divider, current divider, voltage sensor, trans-impedance amplifier, impedance bridge) without deviating from the scope of the present invention.

The change in impedance of the vibrating transducer 200 may be relatively small. Accordingly, the device electronics 300 may include various mechanisms to improve sensitivity of the sensed changes in the impedance. For example, because the impedance between different transducers 200 may vary significantly (based, for example, on the rigidity of the connection between a particular transducer 200 and a particular device 10), each transducer's impedance may be initially calibrated after assembly of the device 10 and the calibration information utilized by the device electronics 300. In another example, the device electronics 300 may record a baseline impedance at the beginning of each drug delivery cycle to correct for variances in the initial impedance between different drug delivery cycles. The measured baseline impedance can be used to recalibrate the device 10 as the baseline impedance shifts over time. The device electronics 300 may then monitor the deviation of the impedance from this baseline to determine when the drug solution 120 is empty or nearly empty. In another example, the shapes, materials, and/or designs of various components of the device 10 disposed in proximity to or between the transducer 200 and drug solution 120 (e.g., the containers 180*a*, 180*b*, 110, the barriers 130, 210, the mediums 160, 230) may be optimized to minimize transducer 200 impedance noise and/or maximize the sensitivity of the impedance of the transducer 200 to the drug solution 120 level.

The illustrated impedance sensor 310 senses drug solution 120 levels through the mediums 160, 230 and barriers 210, 130. The sensor 310 may alternatively be utilized in an ultrasonic nebulizer in which the transducer directly contacts the drug solution 120 without deviating from the scope of the present invention. Use of the impedance sensor 310 in such a nebulizer may facilitate more accurate and/or precise fluid level measurement due to the omission of one or more intermediate layers that might otherwise interfere with the impedance varying interaction between the drug solution 120 and the transducer 200.

The sensor 310 may be used to detect whether coupling medium 160 is disposed between the barriers 130, 210. The absence of coupling medium 160 in the gap between the barriers 130, 210 impairs or prevents the propagation of ultrasonic waves from the transducer 200 to the drug solution 120, which changes the impedance of the transducer 200 relative to when coupling medium 160 is present. The device electronics 300 may therefore use the sensor 310 to detect the absence of coupling medium 160 (e.g., due to failure of the capsule 150 to rupture) and consequently prevent or stop operation of the transducer 200 and device 10 accordingly. The device electronics 300 may warn the patient about the absence of coupling medium 160 between the barriers 130, 210 via any suitable mechanism (e.g., visual or audible warning).

Figure 8:
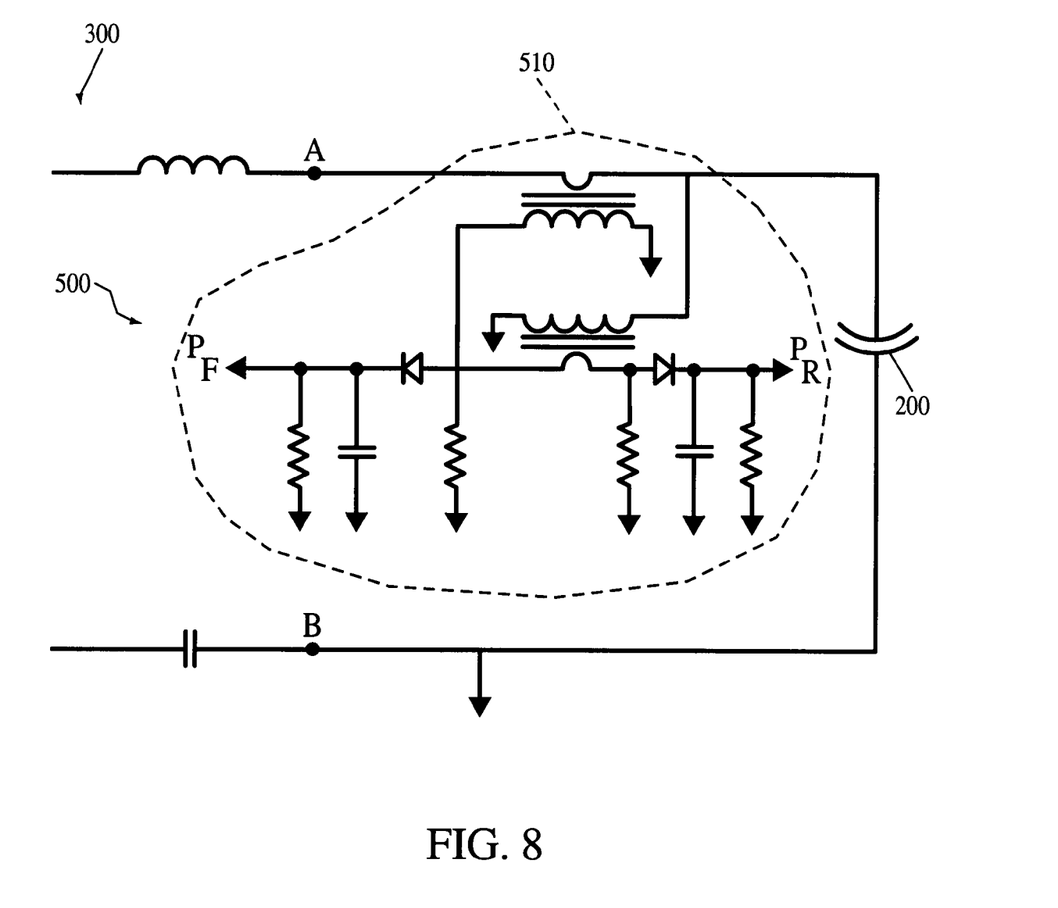

FIG. 8 illustrates an impedance sensor 500 according to an alternative embodiment of the present invention. The impedance sensor 500 comprises a directional coupler 510 that measures an impedance mismatch between the transducer 200 and the device electronics 300 driving the transducer 200. The directional coupler 510 measures a forward power signal $P_F$ of the device electronics 300 relative to a reflected power signal $P_R$ that is reflected back from the transducer 200 toward the device electronics 300. When the impedance of the transducer 200 is close to the output impedance of the device electronics, a minimum of power $P_R$ is reflected back. As the transducer 200 impedance changes, more power is reflected back and $P_R$ increases. Accordingly, changes in the reflected power signal $P_R$ may be used to detect changes in the impedance of the transducer 200. The device electronics 300 then uses the measured variation in the reflected power signal $P_R$ to determine when the drug solution 120 level falls below a predetermined threshold. While a specific directional coupler 510 is illustrated in FIG. 8, any other suitable directional coupler may alternatively be used without deviating from the scope of the present invention.

Figure 7:
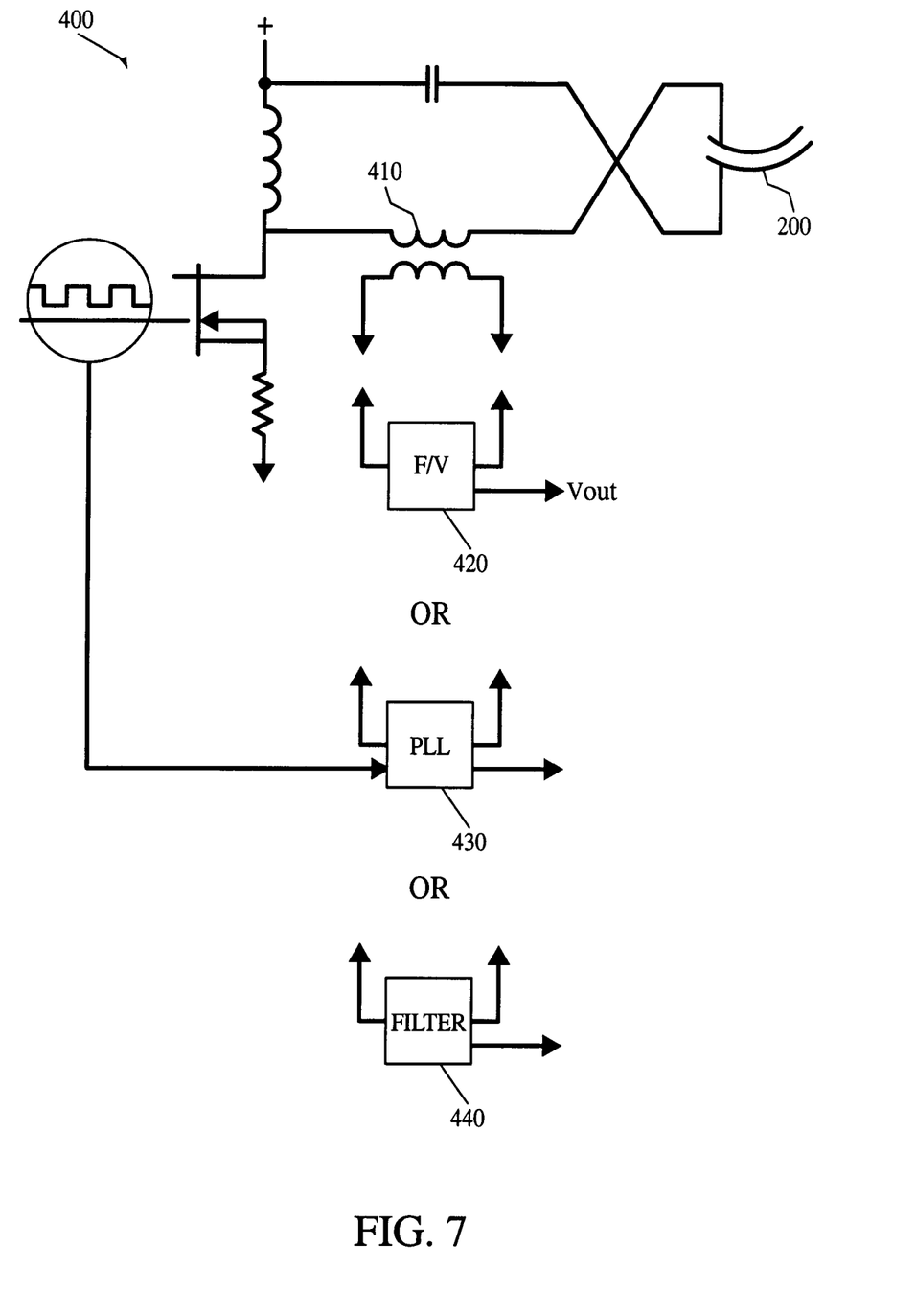

While the illustrated drug solution 120 level sensor 310 senses an impedance of the transducer 200, a drug solution level sensor according to an alternative embodiment of the present invention may determine the drug solution 120 level by measuring any other electrical characteristic of the transducer 200 that is indicative of drug solution 120 level (e.g., frequency or amplitude of transducer 200 oscillation). For example, the resonant frequency or frequencies of the transducer 200 vary as a function of the drug solution 120 level. The function may resemble a linear function, a non-linear function, a step-function, or a combination of these or other functions. Accordingly, as shown in FIG. 7, the device electronics 300 may include a frequency analyzer 400 to detect the frequency shift that results from a drop in the drug solution 120 level. The frequency analyzer 400 is configured to sense a current in the main inductor 410 (or other suitable electrical characteristic at another node of the circuit) connected to the transducer 200 and determines a frequency of the transducer 200. The frequency analyzer 400 may utilize a frequency-to-voltage converter 420 and measure variations in the output voltage $V_{out}$ to sense frequency shifts in the transducer 200, which are indicative of a change in drug solution 120 level. When $V_{out}$ varies by a predetermined amount or reaches a predetermined frequency, the frequency analyzer 400 concludes that the drug solution 120 level has fallen below a predetermined threshold. The device electronics 300 responsively turns off the transducer 200. The frequency analyzer 400 may additionally or alternatively use any other suitable circuitry (e.g., phase-locked-loop filter 430, filter(s) 440) to measure the frequency and/or frequency shifts of the transducer 200. The frequency analyzer 400 may include various components to reduce noise and/or improve sensitivity of the frequency analyzer 400.

In one embodiment, the coupling and transmitting mediums 160, 230 primarily comprise water. In some instances, a sterilant or bactericide, such as alcohol or Benzalkonium chloride, may be added to the mediums 160, 230. The mediums 160, 230 may alternatively comprise any other suitable acoustic wave transmitting mediums (e.g., hydrogel, gel, liquid, or any other relatively viscous or non-viscous fluid, etc.) without deviating from the scope of the present invention.

The concave upper surface of the piezoelectric transducer 200 at least partially comprises silver 205 (e.g., pure silver, a silver oxide, etc.). The silver 205 may form an electrode of the transducer 200. The silver 205 may comprise a coating that covers all or part of the upper surface of the transducer 200. The silver 205 may be applied to the transducer 200 in any suitable manner (e.g., sputter deposition; electroplating; etc.) The transmitting medium 230 is in fluid contact with the silver 205.

The silver 205 gradually corrodes away as it interacts with the transmitting medium 230. Accordingly, the silver 205 is preferably thick enough to endure the such silver loss over a predetermined period of time (e.g., the anticipated lifespan of the device 10). For example, the layer of silver 205 that is exposed to the transmitting medium 230 is preferably at least 8 microns thick, and may be at least 10 microns thick, at least 12 microns thick, about 16 microns thick, or between 9 and 30 microns thick. According to alternative embodiments of the present invention, the metal may be thicker than 30 microns or thinner than 8 microns.

The silver 205 functions as a bactericide by chemically interacting with the transmitting medium 230 to use up oxygen in the transmitting medium 230, thereby depriving any bacteria of the critical oxygen. The bactericidal properties of the silver 205 may facilitate the use of a non-toxic transmitting medium 230 (e.g., water) that does not itself include a sterilant or bactericide. In such an embodiment, if the barriers 130, 210 were ruptured during use, aerosolization of a potentially harmful bactericide or other sterilant could be avoided.

Additional components of the device 10 that contact the mediums 160, 230 or drug solution 120 (e.g., the barriers 130, 210, the upper or lower containers 180a, 180b, the interior and/or exterior walls of the cup module 40, etc.) may also be silver coated to discourage bacteria growth in such mediums. Furthermore, any other surface of the device 10 may also be silver-coated to generally discourage bacteria growth on and in the device 10.

Additionally or alternatively, various components of the device 10 may include an antimicrobial material such as Microban®. The antimicrobial material may be coated onto one or more device 10 components (e.g., the containers 110, 180a, 180b) or integrated into the structure of the components themselves (e.g., by mixing the antimicrobial with plastic or other material that is then molded into the device 10 component).

While the illustrated transducer 200 includes silver to discourage bacteria growth, any other metal having bactericidal properties may be used in addition to or in alternative to silver (e.g., copper) without deviating from the scope of the present invention.

Hereinafter, use of the device 10 is described with reference to FIGS. 1 and 2. With the mouthpiece module 30 detached from the ultrasonic wave generating module 50, a cup module 40 is inserted into the upper container 180a, thereby rupturing the capsule 150 and causing the coupling medium 160 to be disposed between the barriers 130, 210. The seal 125 is pealed away from the cup module 40 to expose the metered dose of drug solution 120 disposed therein. The mouthpiece module 30 is then attached to the remainder of the device 10.

A patient then turns on the device 10, which causes the device electronics 300 to excite the piezoelectric transducer 200. The piezoelectric transducer 200 generates acoustic waves, which propagate sequentially through the transmitting medium 230, the barrier 210, the coupling medium 160, the barrier 130, and the drug solution 120. The drug solution 120 present at the focal point of the acoustic waves will absorb the ultrasonic energy to create a fountain from drug solution 120 present in the reservoir 110. That is, the focused acoustic waves will generate a focused stream of drug solution 120, which stream begins at a point that can also be considered the beginning of the fountain. The fountain extends up through the guide tube 100. Towards the top of the stream or fountain, the energized drug solution 120 within drug solution reservoir 110 is nebulized to form aerosolized drug solution 120 particles. Some of the drug solution 120 in the fountain may not be nebulized, but rather form larger droplets of the drug solution that will be returned to the reservoir 110 via a return channel.

The patient inhales the nebulized drug solution 120 until the drug solution level sensor determines that the treatment cycle is complete and deactivates the transducer 200. The device 10 indicates to the patient that the treatment cycle is complete.

Upon completion of the treatment cycle, the mouthpiece module 30 is detached from the device 10 and the used cup module 40 is detached and discarded. The coupling medium 160 may be emptied from the upper container 180a, or may simply remain in the container 180a and be used in conjunction with the coupling medium 160 of a subsequently used cup module 40. The device 10 may then be used with a new cup module 40 and drug solution 120. Alternatively, a new mouthpiece module 30 may also be used. Alternatively, a patient may reuse the mouthpiece module 30. A plurality of patients may each use their own particular mouthpieces 30 with a common device 10. The disposable cup module 40 facilitates use of the device 10 with different drug solutions 120 and/or by different patients. The cup module 40 may obviate the need for cleaning and/or sterilizing the device 10 between such uses.

According to an alternative embodiment of the present invention, the capsule 150 is omitted from the cup module 40. To use the nebulizer 10, the patient first places a sufficient amount of acoustic wave transmitting medium onto the barrier 210. The patient then inserts a cup module into the upper container 180a such that the deposited transmitting medium facilitates propagation of acoustic waves between the barriers 130, 210.

According to an alternative embodiment of the present invention, the capsule 150 is replaced by a layer of acoustic wave transmitting gel that is disposed on a lower surface of the barrier 130. A release liner may be added to the lower part of the cup module 40 to protect the gel before use. To use the cup module, a patient removes the release liner and inserts the cup module into the container 180a. The gel forms a layer between the barriers 130, 210 that facilitates propagation of acoustic waves between the barriers 130, 210. The cup module and/or cup support may be constructed to place the barriers 130, 210 in very close proximity to each other such that a thin layer of gel is sufficient to propagate acoustic waves between the barriers 130, 210.

According to an alternative embodiment of the present invention, the capsule 150 is replaced by a medium filled container disposed on a lower portion of the cup module. The medium filled container includes a downwardly-facing valve that is normally closed, but is opened upon insertion of the cup module into the cup support. Once open, transmitting medium flows out of the valve and into the gap between the barriers 130, 210. The valve may be a "duck-bill valve." Of course a variety of other valves may alternatively be used without departing from the scope of the present invention (a flap valve, check valve, ball-bearing valve, etc.). The valve abuts a protrusion in the cup support to open the valve when the cup module is inserted into the cup support. Coupling medium 160 then flows out of the container through the valve to fill the gap between the barriers 130, 210. The container preferably includes more medium than is required to fill the gap between the barriers 130, 210, thereby ensuring a sufficient supply of medium to fill the gap. After use of the nebulizer, the cup module is separated from the cup support, which closes the valve and reseals within the container the medium that did not flow out of the container. Resealing the container reduces the amount of medium to be cleaned out of the cup support after use. The medium that flowed into the space between the barriers 130, 210 may be poured out of the cup support after use of the device.

Figure 4:
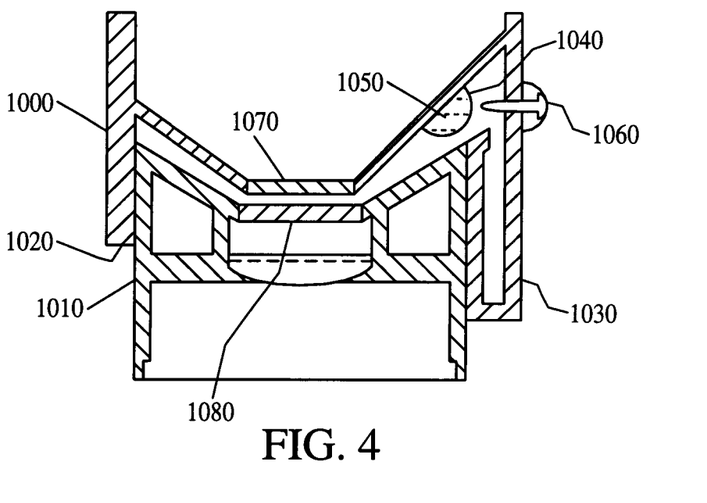

FIG. 4 illustrates a cup module 1000 and cup support 1110 according to an alternative embodiment of the present invention. The device 10 may be modified to accommodate the cup module 1000 and cup support 1110 in place of the cup module 40 and cup support 180 illustrated in FIGS. 1-3.

The cup module 1000 includes a lip 1020 that fits around an outside of a cup support 1010. A collection chamber 1030 extends downwardly within the lip 1020. A capsule 1040 containing a coupling medium 1050 is disposed on an underside of the cup module 1000. A manually-actuatable, sharp projection 1060 extends toward the capsule 1040 from an exterior of the cup module 1000. The housing of the device is arranged such that the projection 1060 is accessible from an exterior of the device.

To use the cup module 1000, the cup module 1000 is placed into the cup support 1010. The projection 1060 is manually pushed by the patient toward the capsule 1040 to rupture the capsule 1040. Rupture of the capsule 1040 releases the coupling medium 1050, which flows into the gap between acoustic wave transmitting barriers 1070, 1080 in the cup module 1000 and cup support 1010. The nebulizer is then operated as discussed above with respect to the device 10. After completion of the drug solution treatment, the patient tilts the nebulizer to the side so that the coupling medium 1050 flows into the collection chamber 1030. The cup module 1000 and used coupling medium 1050 can then be detached from the nebulizer and disposed of.

In the illustrated embodiments, the cup module 40, 1000 is discrete from the mouthpiece module 30. However, according to an alternative embodiment of the present invention, the cup module 40, 1000 and mouthpiece module 30 are integrated into a combined disposable module. A first combined module may be used with a first drug solution by a first patient in connection with the remainder of the device 10 (i.e., the modules 50, 60). The combined module may then be separated from the remainder of the device 10 and a second combined module used with the device 10 for a second patient and/or a second drug solution. The combined module may be a single use module that is disposed of after a single use. Alternatively, the combined module may be assigned to a particular patient such that each patient uses their own combined module with a commonly used remainder of the device. Use of the combined module may eliminate any need to clean and/or sterilize the remainder of the device 10 between uses by a single patient for different drug solutions or by different patients.

Figure 5:
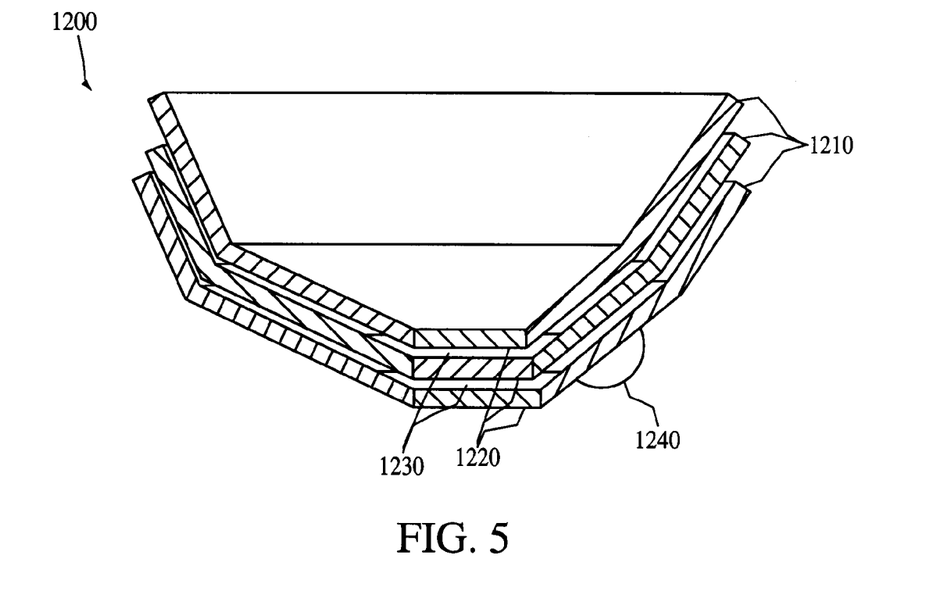

FIG. 5 illustrates an alternative cup module 1200 which may be used with the device 10 in place of the cup module 40. The cup module 1200 comprises a plurality of nested cup liners 1210. Each liner 1210 includes an acoustic wave transmitting barrier 1220. Coupling medium 1230 is disposed between each set of adjacent barriers 1220. A rupturable, coupling medium filled capsule 1240 is disposed on an underside of the lowermost cup liner 1210. To use the cup module 1200, the module 1200 is inserted into the container 180a of the device 10 to rupture the capsule 1240, as discussed above with respect to the cup module 40. Drug solution 120 is placed into the upper-most cup liner 1210. When the device is used, the aerosol generator creates acoustic waves that propagate through the barriers 1220 and coupling medium 1230 into the drug solution 120 in the uppermost liner 1210. After the treatment cycle is completed, the upper-most liner 1210 is separated from the remaining liners 1210, thereby leaving a clean upper liner 1210 ready for subsequent use.

The liners 1210 are preferably nested such that when attached to the device 10, the focal point of the transducer 200 is disposed within drug solution 120 disposed in the uppermost liner 1210 (as opposed to between adjacent liners 1210). The thickness of each liner 1210 may be minimized to increase the number of nested liners 1210 that may be used while still keeping the focal point within the drug solution 120.

While the illustrated embodiments utilize cup modules 40, 1000, the cup module may be omitted entirely without deviating from the scope of the present invention. In such an alternative embodiment, the upper container 180a forms the reservoir that holds the drug solution 120, as shown in U.S. patent application Ser. No. 11/367,486 (now U.S. Publication No. 2006/0201501) and Ser. No. 11/367,075 (now U.S. Publication No. 2006/0243274).

While the illustrated embodiments are designed to aerosolize a liquid drug solution for inhalation by a patient, one or more embodiments of the present invention may alternatively be used to aerosolize a variety of other solutions without deviating from the scope of the present invention (e.g., liquid air freshener, disinfectant, water, etc.).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A nebulizing drug delivery device, comprising:
a drug solution container for holding a drug solution therein;
a transducer connected to the drug solution container and positioned and arranged to generate acoustic waves that move through the drug solution container to nebulize the drug solution, wherein the transducer is a piezoelectric transducer; and
electronics components electrically connected to the transducer, the electronics components being constructed and arranged to provide A/C current to the transducer to drive the transducer, the electronics components comprising a sensor for sensing a sensed electrical characteristic associated with the transducer during operation,
wherein the sensed electrical characteristic associated with the transducer comprises an electrical characteristic that varies as a function of at least the amount of drug solution disposed in the drug solution container,
wherein the electronics components are configured to take a first set of measurements of the electrical characteristic during a first period and determine a first average value for the first set of measurements,
wherein the electronics components are configured to take a second set of measurements of the electrical characteristic during a second period that is subsequent to the first period and determine a second average value for the second set of measurements,
wherein the electronics components are configured to determine a difference between the first average value and the second average value, and
wherein the electronics components are configured to determine that the amount of drug solution disposed in the drug solution container is low, responsive to the difference being greater than a pre-determined threshold.

2. The device of claim 1, wherein the electronics components are constructed and arranged to turn off the transducer when the electrical characteristic reaches a predetermined value.

3. The device of claim 1, wherein the electronics components are constructed and arranged to turn off the transducer responsive to a determination that the amount of drug solution disposed in the drug solution container is low, wherein the determination is responsive to the deviation calculation indicating a change of the electrical characteristic that exceeds a pre-determined threshold.

4. The device of claim 1, wherein the electrical characteristic is indicative of an impedance of the transducer.

5. The device of claim 4, wherein the electronics components are constructed and arranged to turn off the transducer when the electrical characteristic reaches a predetermined value.

6. The device of claim 4, wherein the electronics components are constructed and arranged to turn off the transducer responsive to a determination that the amount of drug solution disposed in the drug solution container is low.

7. The device of claim 1, wherein the transducer is positioned and arranged to generate acoustic waves that move into the drug solution container so that the acoustic waves nebulize a drug solution within the drug solution container.

8. A method of using a nebulizing device, comprising:
operating a piezoelectric transducer to generate acoustic waves to aerosolize a liquid, wherein operating the piezoelectric transducer includes providing A/C current to the piezoelectric transducer;

measuring a sensed electrical characteristic associated with the transducer during operation, wherein the sensed electrical characteristic comprises an electrical characteristic that varies as a function of at least an amount of the liquid disposed in a container;

taking a first set of measurements of the electrical characteristic during a first period;

determining a first average value for the first set of measurements;

taking a second set of measurements of the electrical characteristic during a second period that is subsequent to the first period;

determining a second average value for the second set of measurements;

determining a difference between the first average value and the second average value; and determining, responsive to the difference being greater than a pre-determined threshold, that the amount of drug solution disposed in the drug solution container is low.

9. The method of claim 8, further comprising ceasing operation of the transducer in response to the measured electrical characteristic reaching a predetermined value.

10. The method of claim 8, further comprising ceasing operation of the transducer in response to a determination that the amount of drug solution disposed in the drug solution container is low, wherein the determination is responsive to the deviation calculation indicating a change of the electrical characteristic that exceeds a predetermined threshold.

11. The method of claim 8, wherein the electrical characteristic is indicative of an impedance of the transducer.

12. The method of claim 11, further comprising ceasing operation of the transducer in response to the electrical characteristic reaching a predetermined value.

13. The method of claim 11, further comprising ceasing operation of the transducer responsive to a determination that the amount of drug solution disposed in the drug solution container is low.

14. The method of claim 8, wherein operating the piezoelectric transducer to generate acoustic waves to aerosolize the liquid comprises using the transducer to generate the acoustic waves, and propagating the acoustic waves into the liquid such that the acoustic waves aerosolize the liquid.

* * * * *